US012570984B2

(12) United States Patent
Son

(10) Patent No.: US 12,570,984 B2
(45) Date of Patent: Mar. 10, 2026

(54) DNA APTAMER SPECIFICALLY BINDING TO GLUTATHIONE AND USE THEREOF

(71) Applicant: Nexmos Co., LTD, Seoul (KR)

(72) Inventor: In sik Son, Seongnam-si (KR)

(73) Assignee: NEXMOS Co., Ltd., Seoul (KR)

( * ) Notice: Subject to any disclaimer, the term of this patent is extended or adjusted under 35 U.S.C. 154(b) by 759 days.

(21) Appl. No.: 17/908,669

(22) PCT Filed: Feb. 25, 2021

(86) PCT No.: PCT/KR2021/002371
§ 371 (c)(1),
(2) Date: Sep. 1, 2022

(87) PCT Pub. No.: WO2021/177657
PCT Pub. Date: Sep. 10, 2021

(65) Prior Publication Data
US 2023/0109451 A1 Apr. 6, 2023

(30) Foreign Application Priority Data

Mar. 3, 2020 (KR) ........................ 10-2020-0026698
Feb. 22, 2021 (KR) ........................ 10-2021-0023379

(51) Int. Cl.
*C12N 15/115* (2010.01)
*A61K 8/60* (2006.01)

(52) U.S. Cl.
CPC ............ *C12N 15/115* (2013.01); *A61K 8/606* (2013.01)

(58) Field of Classification Search
None
See application file for complete search history.

(56) References Cited

U.S. PATENT DOCUMENTS

2019/0078094 A1* 3/2019 Son ...................... C12N 15/115

FOREIGN PATENT DOCUMENTS

KR          2018089974      *   8/2018
KR          0202025249      *   3/2020
WO    WO-2020096240 A1 *   5/2020

OTHER PUBLICATIONS

Bala et al. RNA Biology 8, 101-111 (Year: 2011).*
Machine English translation of WO 2020096240, retrieved on May 23, 2025, pp. 1-10 (Year: 2020).*
Escapenet English Translation of KR20200025249, Ahjeongson et al. pp. 1-30 (Year: 2020).*
Escapenet English Translation of KR20180089974, Moon et al. pp. 1-24 (Year: 2018).*
Minich et al. Nutrients 11:2073, pp. 1-20 (Year: 2019).*

* cited by examiner

*Primary Examiner* — Brian Whiteman

(57) ABSTRACT

The present invention relates to a single-stranded DNA aptamer that binds to glutathione to inhibit oxidation of the glutathione or stabilize the glutathione, characterized in that the single-stranded DNA aptamer has one or more stem-loop structures; a method for oxidation prevention and stabilization of glutathione using the aptamer; and application to various fields such as pharmaceuticals, cosmetics, and food, using the aptamer. The aptamer of the present invention can be applied to various fields, such as pharmaceuticals, cosmetics, and food, which require oxidation prevention and stabilization of glutathione.

2 Claims, 5 Drawing Sheets

Specification includes a Sequence Listing.

【FIG. 1】
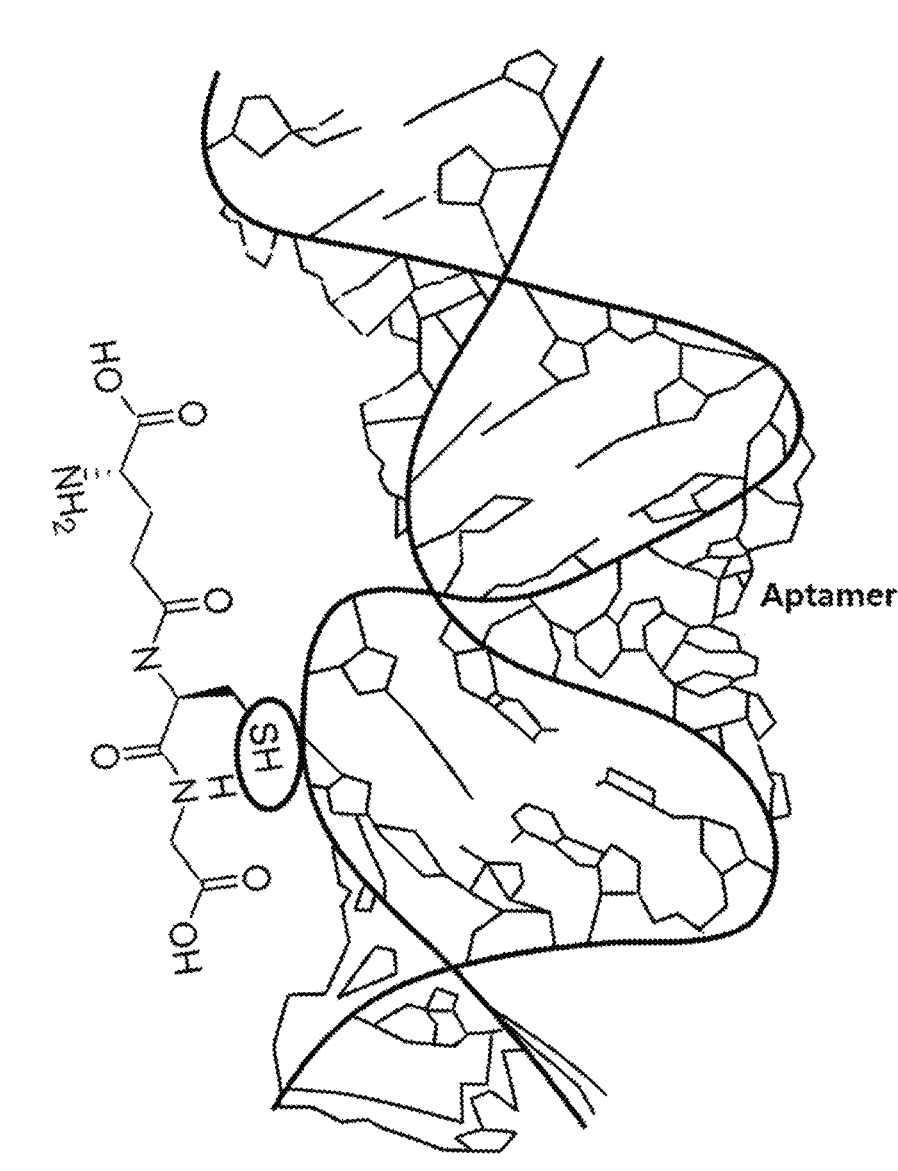
reduced forms of
glutathione
Aptamer

【FIG. 2】
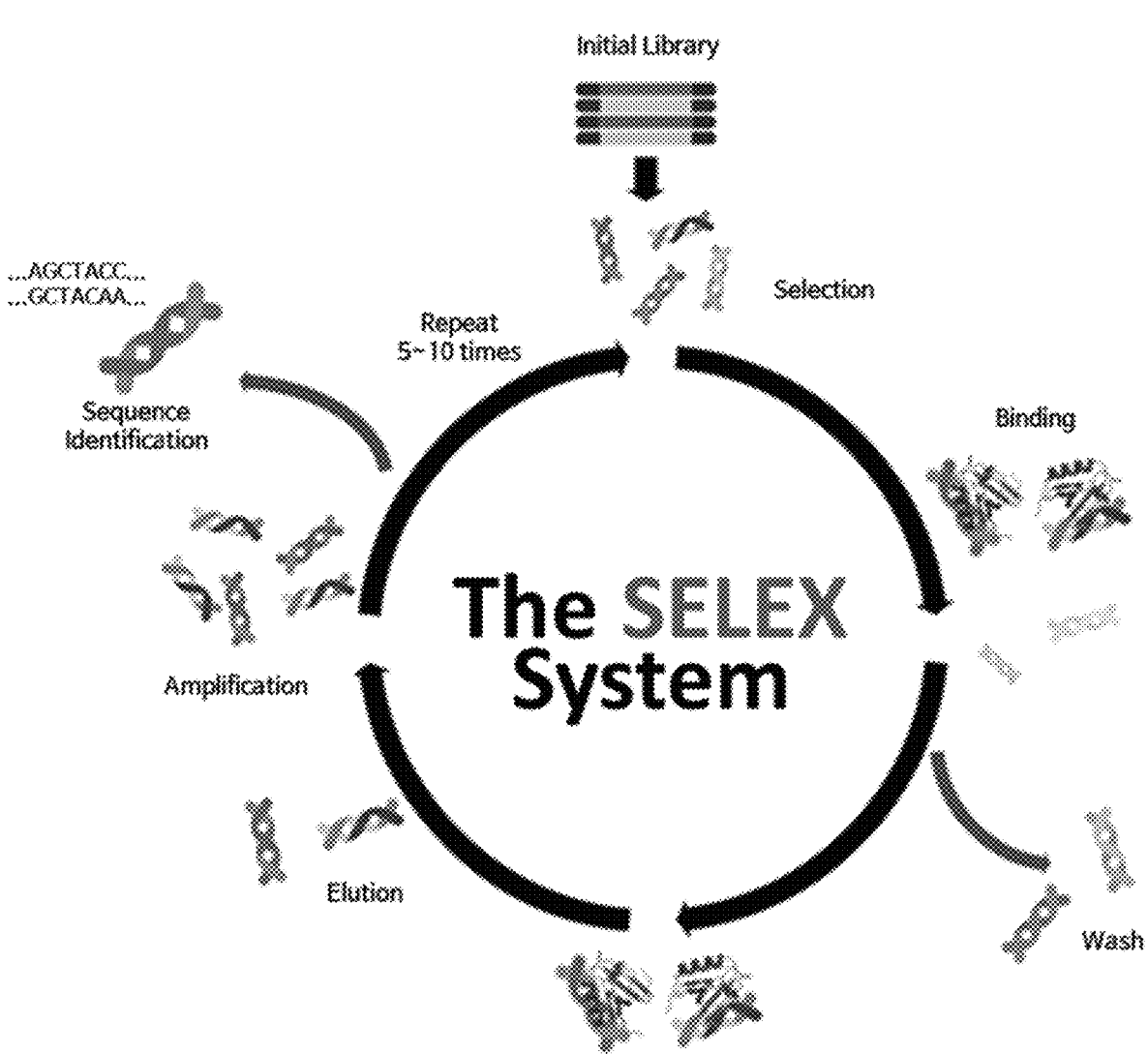

【FIG. 3】
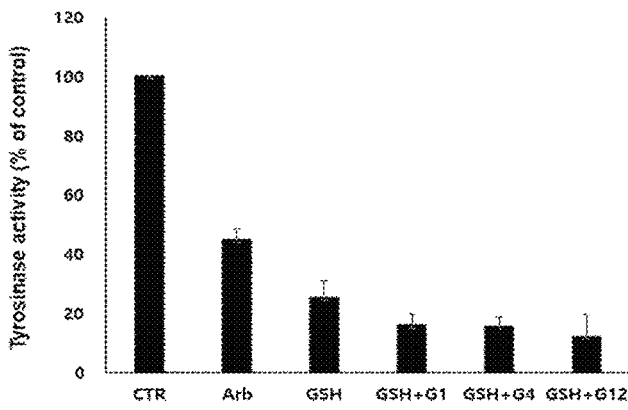

【FIG. 4】
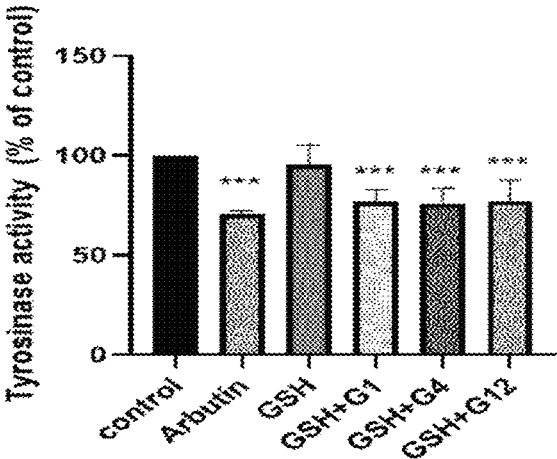

【FIG. 5】
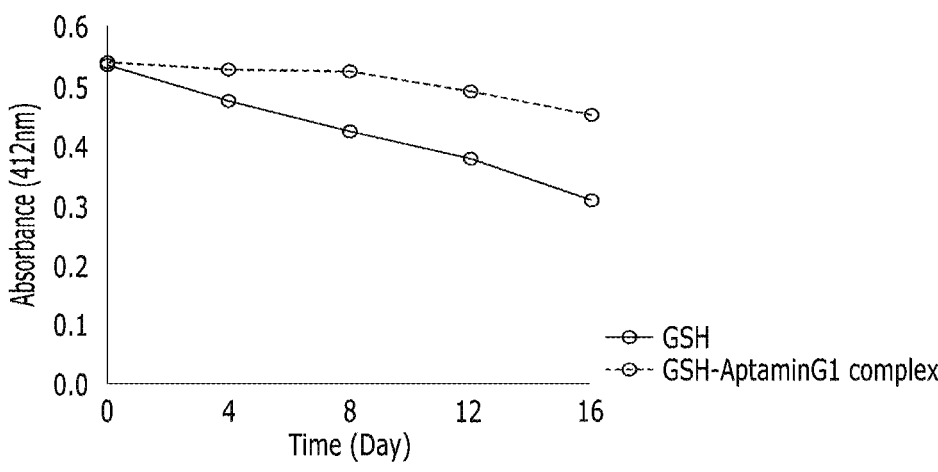
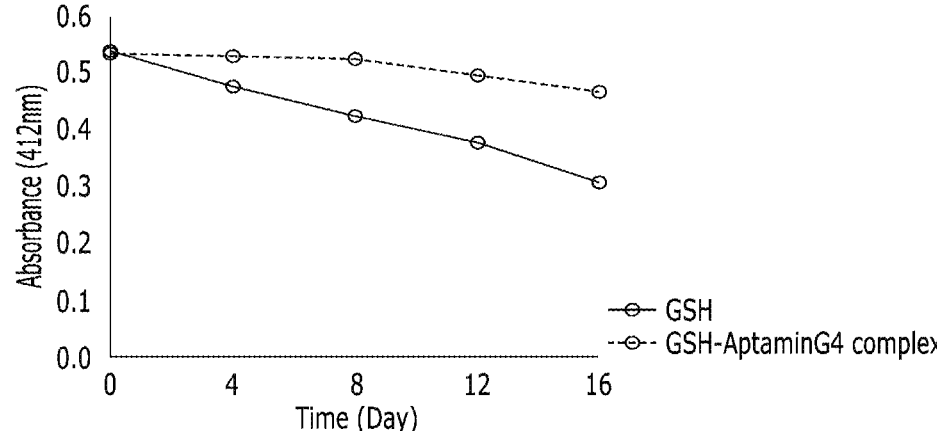
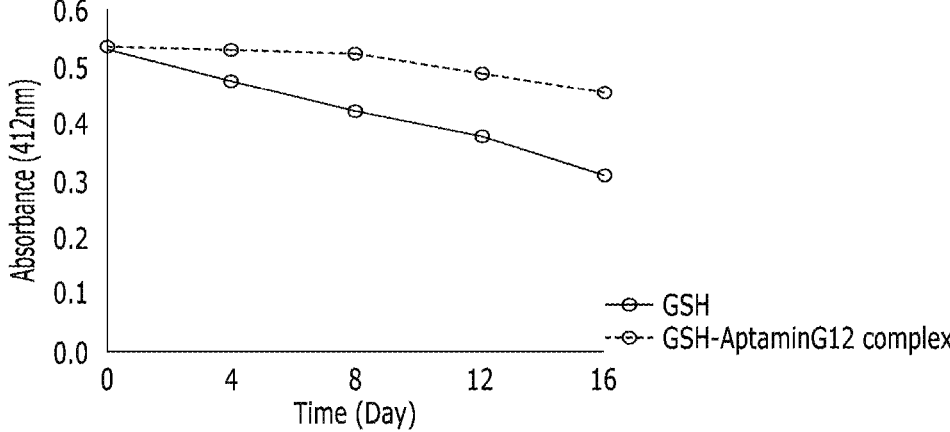

DNA APTAMER SPECIFICALLY BINDING TO GLUTATHIONE AND USE THEREOF

TECHNICAL FIELD

The present invention relates to a DNA aptamer that specifically binds to glutathione and uses thereof, and more particularly, it relates to a DNA aptamer that specifically binds to glutathione, and a method for preventing and stabilizing glutathione oxidation using the aptamer, a method thereof and application in various fields such as pharmaceuticals, cosmetics, and food using aptamers.

BACKGROUND ART

Glutathione (GSH) is a tripeptide composed of three amino acids: glutamine, cysteine, and glycine that prevents damage to important cellular components caused by reactive oxygen species such as free radicals, peroxides, lipid peroxides and heavy metals. It is known as a bio-nutrient with antioxidant, anti-inflammatory, anti-carcinogen, anti-aging and immune function enhancement.

However, the stability of glutathione is inhibited as the thiol group of glutathione (GSH) is easily oxidized to glutathione disulfide (GSSG) over time in a general formulation. Since glutathione has a very low ability to penetrate cell membranes, absorption of glutathione into cells is low, and bioavailability is low due to instability in a neutral or alkaline environment, so there is a problem of low utilization. Therefore, the need for a new method or material for inhibiting the oxidation of glutathione has existed for a long time.

PRIOR PATENT LITERATURE

Republic of Korea Patent Publication No. 10-2018-0054508

DISCLOSURE

Technical Problem

The present invention solves the above problems and is due to the necessity of the above, an object of the present invention is to provide a method for preventing and stabilizing glutathione oxidation.

Another object of the present invention is to provide a substance having an antioxidant action of glutathione.

Another object of the present invention is to provide a substance having a stabilizing action of glutathione.

Another object of the present invention is to provide use as a cosmetic and health functional food using a substance that prevents oxidation of glutathione and has a stabilizing action.

Another object of the present invention is to provide a substance that maintains the reduced state of glutathione and maintains its function for a long period of time through stabilization.

Another object of the present invention is to maintain the reduced state of glutathione and to manufacture cosmetics, health functional foods and foods through a method of maintaining its antioxidant function for a long period of time through stabilization.

Technical Solution

In order to achieve the above object, the present invention provides one aptamer selected from the group consisting of nucleotide sequences set forth in SEQ ID NOs: 1 to 26 that bind to glutathione to inhibit oxidation of glutathione or stabilize glutathione.

The present invention also provides a method for stabilizing glutathione by treating glutathione with the aptamer of the present invention.

The present invention also provides a cosmetic composition comprising the aptamer of the present invention as an active ingredient.

The present invention also provides a food composition comprising the aptamer of the present invention as an active ingredient.

In one embodiment of the present invention, the food is preferably a food selected from the group consisting of beverages, confectionery, candy, dairy products, gums, soybeans, breads, and ice cream, but is not limited thereto.

The present invention also provides a pharmaceutical composition comprising the aptamer of the present invention as an active ingredient.

In the present invention, aptamin is defined as an aptamer that protects an antioxidant. For example, aptamin G is a DNA aptamer that specifically binds to glutathione, and refers to an aptamer that prevents and stabilizes oxidation of glutathione.

1. Aptamin G-Based Cosmetic Application Example

The present invention provides Aptamin G, which is a DNA aptamer that specifically binds to glutathione.

The present invention provides Aptamin G, which is an aptamer that prevents and stabilizes the oxidation of glutathione.

In addition, the present invention provides a cosmetic containing Aptamin G.

In one embodiment of the present invention, the cosmetic containing Aptamin G is preferably characterized by ingredients having skin aging prevention, wrinkle removal, whitening, and moisturizing effects, but is not limited thereto.

In addition, the present invention provides a cosmetic containing Aptamin G prepared by the method of the present invention.

In one embodiment of the present invention, it is characterized in that a specific component is attached to the terminal of the Aptamin G, and the specific component is preferably characterized as a component having skin aging prevention, wrinkle removal, whitening, and moisturizing effects. However, the present invention is not limited thereto.

In addition, the characteristic ingredient of the present invention may be any kind of extract or any raw material used in cosmetics regardless of the active material. For example, green tea extract, licorice extract, mulberry extract, golden extract, pueraria extract, red ginseng extract, good for whitening; apricot extract, oil extract, orange extract, lemon extract, bamboo extract, guava extract, rosemary extract, cornus extract, reishi extract, *Ginkgo biloba* extract, seoshiokyok acid extract, conifer extract and Jaeumdan extract which are good for anti-aging; quince extract, baeknyeoncho extract, paprika extract, aloe extract, loofah extract, and seaweed extract, good for moisturizing; carrot extract, soybean extract, Grapefruit Seed Extract, Grape Seed Extract, and Machibana Extract with antioxidant effect; Caviar, pomegranate, ginseng extract for wrinkle improvement; peach extract and Chunkyung extract for skin regeneration; centella asiatica extract, chamomile extract, ginseng root extract, ginseng extract, angelica extract, good for atopy; mint extract trifolieae Extract, Eoseongcho extract, Peony extract, good for acne; Wood vinegar, Dandelion extract, Calendula extract, Hwangbaek skin extract, Tangja extract, Golden extract, Fennel extract, Compuri extract, good for anti-inflammatory and antibacterial; Yulpi extract and Green tea extract to help pore shrink; glycerin, panthenol, hyaluronic acid, ceramide, beta-glucan, whitening arbutin, vitamin C, whiteness, retinol, astaxanthin, resveratinol, polyphenol, for moisturizing function; elastin, collagen, coenzyme Q10, effectin, and EGF, for elasticity; anti-inflammatory and antibacterial propolis, allantoin, phytostan, infra-acid, antioxidant vitamin E (natural tocopherol), ROE (rosemary oil extract), grapefruit seed extract, etc. are applied.

In addition, the present invention provides a cosmetic composition comprising the Aptamin G of the present invention.

In addition, the present invention is summarized as follows for the use of cosmetic raw materials/materials containing Aptamin G of the present invention.

As is widely known, glutathione is a very unstable substance used as a main material of functional cosmetics, and when exposed to air, it is easily combined with oxygen and decomposed, and its function is quickly lost. It serves to keep the substance as stable as possible by capturing these substances through Aptamin G and inhibiting the binding of these substances with oxygen.

It is a function of controlling the release component of the skin active substance according to the amount of a specific substance secreted from the skin. This technology, called aptasensing, is a method that detects various conditions of the skin in advance and releases substances necessary for the skin according to the condition, and is a method that can be used in various fields such as beauty and treatment. It is possible to implement a system that detects ATP secreted at different concentrations according to the skin temperature, or the aptamer detects cytokines secreted according to the skin condition, and then secretes the skin active ingredients accordingly. Accordingly, by secreting an appropriate amount of an anti-aging substance, it can be designed to control the duration or reduce unnecessary overload on the skin.

Aptamer is a method of detecting a specific substance using the three-dimensional structure of single-stranded DNA or RNA. It is similar to the antigen-antibody reaction, but the size of the substance is much smaller, its activity can be controlled in various ways, and production and storage compared to antibodies. This has the advantage of being easy. Also, unlike an antibody, an aptamer that binds to a chemical substance (glutathione) with a very small size can be synthesized, and it is easy to keep its efficacy constant because it is manufactured by chemical synthesis.

Glutathione (GSH) is a tripeptide composed of three amino acids, glutamine, cysteine, and cysteine, in a reduced form and a thiol group in an oxidized form as glutathione disulfide (GSSG).

The reduced state of glutathione is maintained through the base constituting the aptamer of the present invention and the thiol group of glutathione (FIG. 1).

Glutathione, which binds to Aptamin G of the present invention and maintains a reduced state, can be used in various formulations of cream-type or hydrogel-type skin care compositions and health functional foods containing collagen, elastin, hyaluronic acid, and the like.

The present invention also includes a method of slowly releasing glutathione according to various skin conditions through an aptamer that reacts differently according to skin conditions or external stimuli (eg, ultraviolet rays or skin temperature or acidity) (aptasensing). For example, when the structure of the aptamer changes according to the UV irradiation of the skin, the bound glutathione is released, or when the amount of ATP changes according to the change in the skin temperature or acidity, the structure of the bound Aptamin G changes to release glutathione.

In addition, the present invention includes using in cosmetics of various formulations (serum, gel, lotion, cream, toner, mask pack, etc.) comprising the Aptamin G and glutathione of the present invention as active ingredients.

In one embodiment of the present invention, the cosmetic composition preferably further comprises one or more of collagen, elastin, hyaluronic acid, and a peptide, but is not limited thereto.

2. Health Functional Food Using Aptamin G or Aptamin G and Glutathione Component Complex The present invention provides a health functional food composition comprising the Aptamin G and glutathione complex or Aptamin G of the present invention alone as an active ingredient.

Examples of glutathione suitable for the health functional food of the present invention include glutathione, vitamin A, vitamin C, vitamin D, vitamin E, vitamin K, vitamin B 6, vitamin B 12, thiamine, riboflavin, biotin, folic acid, niacin, pantothenic acid, or mixtures thereof, etc. Examples of suitable mineral nutrients to be included in the dietary supplement composition include those having more than one element selected from sodium, potassium, calcium, magnesium, phosphorus, sulfur, chlorine, iron, copper, iodine, zinc, selenium, manganese, chromium, molybdenum, fluorine, cobalt, and compounds thereof.

Various herbs can also be used as health functional foods. In general, herbs are selected from those with various medicinal or dietary supplement properties. In general, herbs are aromatic plants or parts of plants that can be used medicinally or for flavoring purposes.

In addition, the present invention provides a method of delaying the oxidation rate by binding Aptamin G to glutathione to maintain the reduced state of the antioxidant material including glutathione.

Hereinafter, the present invention will be described.

The present invention, like glutathione, combines antioxidant substances that are very unstable to oxidation, such as Vitamin C, Vitamin A (Retinol), Vitamin E, astaxanthin, resveratinol, polyphenol, coenzyme Q10, Peptide, and Oil, with an aptamer and so it can be manufactured and used as a health function. food. Through this, oxidation (corruption) of the materials is prevented, so that the desired effect of the materials is maintained as much as possible. In addition, it is possible to increase the effect as much as possible by allowing it to be released under a target condition through apta-sensing.

In addition, the present invention provides complex of an aptamer and antioxidant component developed for the antioxidant component or provides an active aptamer and antioxidant component individually.

In one embodiment of the present invention, the antioxidant material comprising glutathione is preferably a material selected from the group consisting of vitamin C, vitamin A, retinol, vitamin E, astaxanthin, resveratrol, 4'-acetoxy resveratrol, catechin, various polyphenols, epigallocatechin gallate, coenzyme Q10, ubiquinol, ubiquinone, omega 3, and oil, but is not limited thereto.

3. Food, Beverage and Food Composition Using Aptamin G and/or Aptamin G and Glutathione Component Complex The present invention provides a beverage composition comprising the Aptamin G and Aptamin G and glutathione complex of the present invention as an active ingredient or Aptamin G alone in the beverage.

In one embodiment of the present invention, the composition preferably further comprises one or more of collagen, elastin, hyaluronic acid, and a peptide, but is not limited thereto.

The present invention also provides a food composition comprising the aptamer and/or antioxidant of the present invention as an active ingredient.

In one embodiment of the present invention, the food composition preferably further comprises one or more of collagen, elastin, hyaluronic acid, and a peptide, but is not limited thereto.

In one embodiment of the present invention, the food composition is preferably confectionery, candy, dairy product, gum, or paste, bread, or ice cream, but is not limited thereto.

The present invention also provides a method for preparing food by adding the Aptamin G of the present invention to food.

In another embodiment of the present invention, it is preferred that the food and beverage composition is absorbed into the body and releases glutathione when the structure of Aptamin G is changed, or when the amount of ATP is changed according to changes in the environment in the body, the structure of Aptamin G is changed to release glutathione but is not limited thereto.

In addition, preventing and stabilizing the oxidation of glutathione using an aptamer is a safe and innovative new concept approach compared to the existing method, and it can be manufactured to maximize the effect by applying it to various industries.

In particular, it will be a trigger for transforming the existing chemical-based cosmetics, food, animal, and pharmaceutical markets into a DNA-based market. It is also used in various fields such as various industries. In the future, it is expected to provide an explosive increase in the DNA market and innovative solutions.

4. Pharmaceutical Composition Using Aptamer G or Aptamer G and Glutathione Complex When the composition of the present invention is a pharmaceutical composition, it can be used for applications showing the pharmacological effect of glutathione mentioned in the background art. For administration of the composition of the present invention, a pharmaceutically acceptable carrier, excipient or diluent may be included in addition to the active ingredients described above. The carrier, excipient and diluent include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oil.

The pharmaceutical composition of the present invention can be formulated and used in the form of oral dosage forms such as powders, granules, tablets, capsules, suspensions, emulsions, syrups, aerosols, external preparations, suppositories, or sterile injection solutions, respectively, according to conventional methods. In detail, when formulating, it may be prepared using a diluent or excipient such as a filler, a weight agent, a binder, a wetting agent, a disintegrant, and a surfactant commonly used. Solid preparations for oral administration include, but are not limited to, tablets, pills, powders, granules, capsules, and the like. Such a solid preparation may be prepared by mixing at least one or more excipients, for example, starch, calcium carbonate, sucrose, lactose, gelatin, etc. in addition to the active ingredient. In addition to simple excipients, lubricants such as magnesium stearate and talc may also be used. It can be prepared by adding various excipients, for example, wetting agents, sweetening agents, fragrances, preservatives, and the like, in addition to liquids for oral use and liquid paraffin. Formulations for parenteral administration include sterile aqueous solutions, non-aqueous solvents, suspensions, emulsions, lyophilized formulations, and tasks. As the non-aqueous solvent and suspending agent, propylene glycol, polyethylene glycol, vegetable oils such as olive oil, and injectable esters such as ethyl oleate may be used. As the base of the suppository, Witepsol, Macrosol, Tween 61, cacao butter, laurin fat, glycerogelatin, etc. may be used.

A suitable dosage of the pharmaceutical composition of the present invention varies depending on the patient's condition and weight, the severity of the disease, the drug form, and time, but may be appropriately selected by those skilled in the art. The daily dose of the composition is preferably 0.001 mg/kg body weight to 500 mg/kg body weight, and may be administered once a day or divided into several times a day as needed.

Advantageous Effects

As can be seen through the present invention, the aptamer of the present invention has an antioxidant and stabilizing effect of glutathione, and the aptamer of the present invention regulates the release rate of the skin active ingredient, and a specific substance secreted from the skin. It is expected to have a function of regulating the release component of the antioxidant according to the amount.

The aptamer of the present invention has an antioxidant effect of an antioxidant such as glutathione, and the aptamer alone or the complex of aptamer and glutathione of the present invention maintains the reduced state of glutathione using, for example, an aptamer that selectively binds to glutathione to maintain its antioxidant function for a long period of time and so it can be used for functional foods and foods. By using an aptamer that selectively binds to glutathione, continuous and maximized antioxidant and stabilizing effects can be expected even with a small amount of glutathione.

In addition, as can be seen from the present invention, the present invention uses an aptamer that selectively binds to glutathione to maintain the reduced state of physiologically active ingredients such as glutathione and maintains its antioxidant and stabilizing functions for a long period of time and so it can be used in beverages and antioxidant foods.

In addition, antioxidation and stabilization of glutathione using an aptamer is a safe and innovative new concept approach compared to the existing method, and it can be manufactured so that the effect can be seen by applying it to various industries. In particular, it will be a trigger for transforming the existing chemical-based cosmetics, health functional food, food, animal, and pharmaceutical markets into a DNA-based market. It is expected to provide an explosive increase in the DNA market and innovative solutions in the future.

DESCRIPTION OF DRAWINGS

FIG. 1 is a diagram of maintaining a stable state of glutathione through hydrogen bonding between the base constituting the aptamer and the thiol group of glutathione.

FIG. 2 shows the SELEX process for producing an aptamer that specifically binds to glutathione.

FIG. 3 is a graph confirming the Tyrosinase activity rate of Aptamin G1 (SEQ ID NO: 24), Aptamin G4 (SEQ ID NO: 25), Aptamin G12 (SEQ ID NO: 26) that specifically binds to GSH;

FIG. 4 is a graph confirming the tyrosinase activity rate of GSH-specific binding Aptamin G1 (SEQ ID NO: 17), Aptamin G4 (SEQ ID NO: 18), Aptamin G12 (SEQ ID NO: 19) by a cell test, FIG. 5 is a graph of the antioxidant efficacy test (DTNB assay) of Aptamin G1 (SEQ ID NO: 24), Aptamin G4 (SEQ ID NO: 25), and Aptamin G12 (SEQ ID NO: 26) that specifically binds to GSH.

MODE FOR INVENTION

Hereinafter, the present invention will be described in more detail by the following examples. However, the following examples are described with the intention of illustrating the present invention, and the scope of the present invention is not to be construed as being limited by the following examples.

In the present invention, in order not to rapidly oxidize the target (glutathione), all buffers and solutions were stirred in Chelex®100 resin (BioRad) for 1 hour, filtered through a 0.2 μm filter, and sprayed with $N_2$ gas (Praxair) for 10 minutes. Thus, it was prepared using molecular biology grade water (Phenix Research) from which incidental metals were removed.

Example 1: DNA Aptamer Selection and Sequencing

Glutathione SELEX

Nine rounds of SELEX against glutathione were performed using a DNA library composed of $\sim 10^{15}$ unique oligonucleotides. The buffer composition used was as follows: 50 mM Sodium Acetate pH 5.5 (Sigma), Phosphate-buffered saline (PBS) with 1 mM $MgCl_2$, 0.05% Tween 20 (Sigma), 1% BSA (Sigma) and 1 mM glutathione (Sigma). The stringency of SELEX was changed by reducing the binding time of the aptamer to the target, changing the buffer composition, and reducing the concentration of the target in free molecule elution (FIG. 2).

DNA Aptamer Selection

Bioinformation analysis of the abundant library produced by the SELEX method obtained candidate aptamers, screened for the ability to protect glutathione from oxidation from these top 26, and the results are shown in Table 1 below.

8

TABLE 1

| SEQ ID NO: | selected sequence | sequence size (bp) |
|---|---|---|
| 1 | GACCAACGGAAGCGCGGCACCACA ACGGTG | 30 |
| 2 | CGAACAGCATGGAGGCGCGCCCGT TGTGCCGTGCGCGCGGGAT | 43 |
| 3 | GGCACGCAGTGTGACGCGCCTCGT CGTTCACTCGGCGCGGGAT | 43 |
| 4 | GCACGGCACAACGGGCGCGCCTCC ATGCTGTTCGGCGCGGGAT | 43 |
| 5 | CGAGTGAACGACGAGGCGCGTCAC ACTGCGTGCCGCGCGGGAT | 43 |
| 6 | CGAGTCAGTGCGAGGCGCTCCCCT GTCGGTGCGCGCGGGAT | 41 |
| 7 | GCACCGACAGGGGAGCGCCTCGCA CTGACTCGGCGCGGGAT | 41 |
| 8 | ACGCATGCCGGGCGCGCTCCCTGTC GTCCGCGCGGGAT | 38 |
| 9 | CGACTACGAGGAGGCGCGCACCAC ACGTT | 29 |
| 10 | AACGTACGTGGAGCGGCTCCCTGC ACTGCGCGCGGGAT | 38 |
| 11 | GCAGTGCAGGGAGCCGCTCCACGT ACGTTGCGCGGGAT | 38 |
| 12 | GGTCTGCCGGGGCCGCACCTCCTGT CGTCGGCGCGGGAT | 39 |
| 13 | GCACAATCGGGGCGCGCTCGTCCTC TGGCCGGCGCGGGAT | 40 |
| 14 | CGGCCAGAGGACGAGCGCGCCCCG ATTGTGCGCGCGGGAT | 40 |
| 15 | GGACGACAGGGAGCGCGCCC | 20 |
| 16 | CGACGACAGGAGGTGCGGCCCCGG CAGACCGCGCGGGAT | 39 |
| 17 | CGAGTGAGGGCGAGGCGCGACGTC CCTTCGGTCCGCGCGGGAT | 43 |
| 18 | CGAGTCAGTGCGAGGCGCGCTCCT GCCGTTGCGCGCGGGAT | 41 |
| 19 | GGACCGAAGGGACGTCGCGCCTCG CCCTCACTCGGCGCGGGAT | 43 |
| 20 | CGACGGAGGGAGGCGCGCACCACA CGTT | 28 |
| 21 | GACCAACGGAGCGCGGCCCACAAC GGT | 27 |
| 22 | GACATCAGGAGCGCGCCCCGTCAC G | 25 |
| 23 | GACCAACGGAGCGCGGCCCACAAC GGTG | 28 |
| 24 | CGAACAGCATGGAGGCGCGCCCGT TGTGCCGTGC | 34 |

TABLE 1-continued

| SEQ ID NO: | selected sequence | sequence size (bp) |
|---|---|---|
| 25 | CGAGTGAACGACGAGGCGCGTCAC ACTGCG | 30 |
| 26 | GGACGACAGGGAGCGCGCCCGGCA TGCGTG | 30 |

Example 2: Whitening Efficacy Test In Vitro Tyrosinase Activity (N=5)

The final concentrations of each component in this experiment were 20 μM GSH, 0.2 μM Apt G, and 0.01% arbutin.

The experimental method is as follows.

After dissolving in $3^{th}$ distilled water that reacts specifically with GSH (glutathione) obtained through the SELEX, it was boiled at 95° C. for 5 minutes, and then the temperature was gradually lowered to room temperature to form a tertiary structure.

300 μM GSH and 3 μM of the prepared aptamer (molar concentration of 100:1) were dissolved in tertiary distilled water and reacted at room temperature for 30 minutes.

In a 96 well plate, 200 μL of 0.1 M potassium phosphate buffer (pH6.5), 20 μL of sample, 20 μL of 2 KU/mL tyrosinase, and 60 μL of 1.0 mM tyrosine were sequentially added and reacted at 37° C. for 10 minutes.

After the reaction, absorbance was measured at 490 nm using a plate reader.

The results are shown in FIG. 3. FIG. 3 is a graph confirming the Tyrosinase activity rate of Aptamin G1 (SEQ ID NO: 24), Aptamin G4 (SEQ ID NO: 25), Aptamin G12 (SEQ ID NO: 26) that specifically binds to GSH, As a result of FIG. 3, it was confirmed that GSH inhibited the activity of tyrosinase by about 75%, and when complex with the Aptamin G sequence, it was confirmed that the inhibition of tyrosinase activity of GSH was increased by more than 10%.

For reference, the G1 sequence used in the present invention, SEQ ID NO: 24: CGAACAGCATG-GAGGCGCGCCCGTTGTGCCGTGC, is a part of SEQ ID NO: 2 in the present invention.

The G4 sequence, SEQ ID NO: 25: CGAGT-GAACGACGAGGCGCGTCACACTG CG, is part of SEQ ID NO:5 in the present invention.

Example 3: Whitening Efficacy Test In Vitro Cell-Based Tyrosinase Activity (N=5, Arb Only N=3)

The final concentration of each component in this experiment was 100 μM GSH, 1 μM Apt G, 0.01% arbutin, The experimental method is as follows.

After dissolving in $3^{th}$ distilled water that reacts specifically with GSH (glutathione) obtained through the SELEX, it was boiled at 95° C. for 5 minutes, and then the temperature was gradually lowered to room temperature to form a tertiary structure. 100 μM GSH and 1 μM of the prepared aptamer (molar concentration of 100:1) were added to the media and reacted at room temperature for 30 minutes.

MNT-1 cells were seeded on a 6-well plate and incubated for 24 hours at 37° C., 5% $CO_2$ incubator.

After treating each of the prepared samples, the samples were again incubated at 37° C. and 5% $CO_2$ incubator for 72 hours.

After incubation, ice-cold lysis buffer (RIPA buf.+ protease inhibitor) was used to remove the cells from the plate, and the removed cells were transferred to an EP-tube and centrifuged to remove only the supernatant.

Lysate, L-DOPA, potassium phosphate buffer (pH6.5) was added to a 96 well plate and mixed (each test group used the same amount of protein through protein quantification).

After incubation for 1 hour at 37° C., 5% $CO_2$ incubator, absorbance was measured at 475 nm using a plate reader.

The results are shown in FIG. 4.

FIG. 4 is a graph confirming the tyrosinase activity rate of Aptamin G1 (SEQ ID NO: 24), Aptamin G4 (SEQ ID NO: 25), and Aptamin G12 (SEQ ID NO: 26) that specifically binds to GSH by cell test;

As a result of FIG. 4, GSH showed a tendency not to inhibit the activity of tyrosinase, and when complexed with the Aptamin G sequence, it inhibited about 25% of the tyrosinase activity of GSH, which had similar inhibitory efficacy as 0.01% Arbutin, a positive control. visible was confirmed.

Example 4: Antioxidant Efficacy Test DTNB Assay (Sulfhydryl Group (—SH) Determination, n=5)

In this experiment, the final concentration of each component was 125 μM GSH and 1.25 μM aptamin G.

The experiment is as follows.

After dissolving in 3th distilled water that reacts specifically with GSH (glutathione) obtained through the SELEX, and then boiled at 95° C. for 5 minutes, and then slowly lowered the temperature to the room temperature to form a tertiary structure.

The prepared aptamer (100:1) of the prepared aptamer (100:1) of 250 μM GSH and 2.5 μM was dissolved in the $3^{th}$ distilled water for 30 minutes at room temperature.

The above GSH-Aptamin G complex was stored for a certain period of time under severe conditions (37° C.), and samples were obtained every 4 days and measured for 16 days.

Just before the sample measurement, 10 mm DTNB (4 mg/ml, buffer: 0.1 M potassium Phosphate buffer, pH 8.0) was prepared to mix the sample (50 μL) of DTNB solution and shaking incubation.

After the reaction, the UV Absorbance value was measured at 412 nm and REF wavelength 605 nm using the Plate Reader.

The result was shown in FIG. 5.

FIG. 5 is an antioxidant efficacy test of Aptamin G1 (SEQ ID NO: 24), Aptamin G4 (SEQ ID NO: 25), and Aptamin G12 (SEQ ID NO: 26).

As a result of FIG. 5, the GSH was steadily oxidized for 16 days, and the amount of GSH remaining was about 60%, but on day 16, it was confirmed that about 85% or more of GSH remained unoxidized by Aptamins G1, G4, and G12 (aptamers of SEQ ID NOs: 24, 25 and 26, respectively).

The invention claimed is:

1. A DNA aptamer selected from the group consisting of the nucleotide sequences set forth in SEQ ID NOs: 2 to 26 that binds to glutathione to inhibit oxidation of glutathione or stabilize glutathione.

2. A cosmetic composition comprising the aptamer of claim 1 as an active ingredient.

\* \* \* \* \*

SEQUENCE LISTING

<160> NUMBER OF SEQ ID NOS: 26

<210> SEQ ID NO 1
<211> LENGTH: 30
<212> TYPE: DNA
<213> ORGANISM: Artificial Sequence
<220> FEATURE:
<223> OTHER INFORMATION: aptamer

<400> SEQUENCE: 1
gaccaacgga agcgcggcac cacaacggtg                                      30

<210> SEQ ID NO 2
<211> LENGTH: 43
<212> TYPE: DNA
<213> ORGANISM: Artificial Sequence
<220> FEATURE:
<223> OTHER INFORMATION: aptamer

<400> SEQUENCE: 2
cgaacagcat ggaggcgcgc ccgttgtgcc gtgcgcgcgg gat                       43

<210> SEQ ID NO 3
<211> LENGTH: 43
<212> TYPE: DNA
<213> ORGANISM: Artificial Sequence
<220> FEATURE:
<223> OTHER INFORMATION: aptamer

<400> SEQUENCE: 3
ggcacgcagt gtgacgcgcc tcgtcgttca ctcggcgcgg gat                       43

<210> SEQ ID NO 4
<211> LENGTH: 43
<212> TYPE: DNA
<213> ORGANISM: Artificial Sequence
<220> FEATURE:
<223> OTHER INFORMATION: aptamer

<400> SEQUENCE: 4
gcacggcaca acgggcgcgc ctccatgctg ttcggcgcgg gat                       43

<210> SEQ ID NO 5
<211> LENGTH: 43
<212> TYPE: DNA
<213> ORGANISM: Artificial Sequence
<220> FEATURE:
<223> OTHER INFORMATION: aptamer

<400> SEQUENCE: 5
cgagtgaacg acgaggcgcg tcacactgcg tgccgcgcgg gat                       43

<210> SEQ ID NO 6
<211> LENGTH: 41
<212> TYPE: DNA
<213> ORGANISM: Artificial Sequence
<220> FEATURE:
<223> OTHER INFORMATION: aptamer

<400> SEQUENCE: 6
cgagtcagtg cgaggcgctc ccctgtcggt gcgcgcggga t                        41

<210> SEQ ID NO 7
<211> LENGTH: 41
<212> TYPE: DNA
<213> ORGANISM: Artificial Sequence

```
<220> FEATURE:
<223> OTHER INFORMATION: aptamer

<400> SEQUENCE: 7
gcaccgacag gggagcgcct cgcactgact cggcgcggga t                          41

<210> SEQ ID NO 8
<211> LENGTH: 38
<212> TYPE: DNA
<213> ORGANISM: Artificial Sequence
<220> FEATURE:
<223> OTHER INFORMATION: aptamer

<400> SEQUENCE: 8
acgcatgccg ggcgcgctcc ctgtcgtccg cgcgggat                             38

<210> SEQ ID NO 9
<211> LENGTH: 29
<212> TYPE: DNA
<213> ORGANISM: Artificial Sequence
<220> FEATURE:
<223> OTHER INFORMATION: aptamer

<400> SEQUENCE: 9
cgactacgag gaggcgcgca ccacacgtt                                       29

<210> SEQ ID NO 10
<211> LENGTH: 38
<212> TYPE: DNA
<213> ORGANISM: Artificial Sequence
<220> FEATURE:
<223> OTHER INFORMATION: aptamer

<400> SEQUENCE: 10
aacgtacgtg gagcggctcc ctgcactgcg cgcgggat                             38

<210> SEQ ID NO 11
<211> LENGTH: 38
<212> TYPE: DNA
<213> ORGANISM: Artificial Sequence
<220> FEATURE:
<223> OTHER INFORMATION: aptamer

<400> SEQUENCE: 11
gcagtgcagg gagccgctcc acgtacgttg cgcgggat                             38

<210> SEQ ID NO 12
<211> LENGTH: 39
<212> TYPE: DNA
<213> ORGANISM: Artificial Sequence
<220> FEATURE:
<223> OTHER INFORMATION: aptamer

<400> SEQUENCE: 12
ggtctgccgg ggccgcacct cctgtcgtcg gcgcgggat                            39

<210> SEQ ID NO 13
<211> LENGTH: 40
<212> TYPE: DNA
<213> ORGANISM: Artificial Sequence
<220> FEATURE:
<223> OTHER INFORMATION: aptamer

<400> SEQUENCE: 13
gcacaatcgg ggcgcgctcg tcctctggcc ggcgcgggat                           40
```

-continued

```
<210> SEQ ID NO 14
<211> LENGTH: 40
<212> TYPE: DNA
<213> ORGANISM: Artificial Sequence
<220> FEATURE:
<223> OTHER INFORMATION: aptamer

<400> SEQUENCE: 14
cggccagagg acgagcgcgc cccgattgtg cgcgcgggat                              40

<210> SEQ ID NO 15
<211> LENGTH: 20
<212> TYPE: DNA
<213> ORGANISM: Artificial Sequence
<220> FEATURE:
<223> OTHER INFORMATION: aptamer

<400> SEQUENCE: 15
ggacgacagg gagcgcgccc                                                    20

<210> SEQ ID NO 16
<211> LENGTH: 39
<212> TYPE: DNA
<213> ORGANISM: Artificial Sequence
<220> FEATURE:
<223> OTHER INFORMATION: aptamer

<400> SEQUENCE: 16
cgacgacagg aggtgcggcc ccggcagacc gcgcgggat                               39

<210> SEQ ID NO 17
<211> LENGTH: 43
<212> TYPE: DNA
<213> ORGANISM: Artificial Sequence
<220> FEATURE:
<223> OTHER INFORMATION: aptamer

<400> SEQUENCE: 17
cgagtgaggg cgaggcgcga cgtcccttcg gtccgcgcgg gat                          43

<210> SEQ ID NO 18
<211> LENGTH: 41
<212> TYPE: DNA
<213> ORGANISM: Artificial Sequence
<220> FEATURE:
<223> OTHER INFORMATION: aptamer

<400> SEQUENCE: 18
cgagtcagtg cgaggcgcgc tcctgccgtt gcgcgcggga t                            41

<210> SEQ ID NO 19
<211> LENGTH: 43
<212> TYPE: DNA
<213> ORGANISM: Artificial Sequence
<220> FEATURE:
<223> OTHER INFORMATION: aptamer

<400> SEQUENCE: 19
ggaccgaagg gacgtcgcgc ctcgccctca ctcggcgcgg gat                          43

<210> SEQ ID NO 20
<211> LENGTH: 28
<212> TYPE: DNA
<213> ORGANISM: Artificial Sequence
<220> FEATURE:
<223> OTHER INFORMATION: aptamer
```

-continued

<400> SEQUENCE: 20
cgacggaggg aggcgcgcac cacacgtt                                          28

<210> SEQ ID NO 21
<211> LENGTH: 27
<212> TYPE: DNA
<213> ORGANISM: Artificial Sequence
<220> FEATURE:
<223> OTHER INFORMATION: aptamer

<400> SEQUENCE: 21
gaccaacgga gcgcggccca caacggt                                          27

<210> SEQ ID NO 22
<211> LENGTH: 25
<212> TYPE: DNA
<213> ORGANISM: Artificial Sequence
<220> FEATURE:
<223> OTHER INFORMATION: aptamer

<400> SEQUENCE: 22
gacatcagga gcgcgccccg tcacg                                            25

<210> SEQ ID NO 23
<211> LENGTH: 28
<212> TYPE: DNA
<213> ORGANISM: Artificial Sequence
<220> FEATURE:
<223> OTHER INFORMATION: aptamer

<400> SEQUENCE: 23
gaccaacgga gcgcggccca caacggtg                                         28

<210> SEQ ID NO 24
<211> LENGTH: 34
<212> TYPE: DNA
<213> ORGANISM: Artificial Sequence
<220> FEATURE:
<223> OTHER INFORMATION: Aptamer

<400> SEQUENCE: 24
cgaacagcat ggaggcgcgc ccgttgtgcc gtgc                                  34

<210> SEQ ID NO 25
<211> LENGTH: 30
<212> TYPE: DNA
<213> ORGANISM: Artificial Sequence
<220> FEATURE:
<223> OTHER INFORMATION: Aptamer

<400> SEQUENCE: 25
cgagtgaacg acgaggcgcg tcacactgcg                                       30

<210> SEQ ID NO 26
<211> LENGTH: 30
<212> TYPE: DNA
<213> ORGANISM: Artificial Sequence
<220> FEATURE:
<223> OTHER INFORMATION: Aptamer

<400> SEQUENCE: 26
ggacgacagg gagcgcgccc ggcatgcgtg                                       30